United States Patent [19]

Sugiyama

[11] Patent Number: 5,026,281
[45] Date of Patent: Jun. 25, 1991

[54] DENTAL INSTRUMENT FOR PREVENTING ACCIDENTAL SWALLOW

[76] Inventor: Masahiro Sugiyama, 32-8, Kurobaru 2-chome, Kokurakita-ku, Kitakyushu-shi, Fukuoka, Japan

[21] Appl. No.: 444,240

[22] Filed: Dec. 1, 1989

[30] Foreign Application Priority Data

Dec. 14, 1988 [JP] Japan .................. 63-163003[U]
Aug. 25, 1989 [JP] Japan .................. 1-99261[U]

[51] Int. Cl.⁵ ............................... A61B 1/24
[52] U.S. Cl. ............................. 433/30; 433/31
[58] Field of Search ..................... 433/30, 31, 97

[56] References Cited

U.S. PATENT DOCUMENTS

| 911,659 | 2/1909 | Kleberg | 433/30 |
| 1,345,718 | 7/1920 | Underwood | 433/30 |
| 2,434,311 | 1/1948 | Dean | 433/30 |
| 2,436,040 | 2/1948 | Friedman | 433/30 |

FOREIGN PATENT DOCUMENTS 1440561  6/1976  United Kingdom ................. 433/30

Primary Examiner—Gene Mancene
Assistant Examiner—Michael Lynch
Attorney, Agent, or Firm—Armstrong, Nikaido, Marmelstein, Kubovcik & Murray

[57] ABSTRACT

A dental instrument to prevent accidentally swallowing a filler, etc. has a circumferential wall for drop prevention mounted on the periphery of a receiving plate. A grip is attached to the receiving plate or circumferential wall. The dental instrument is inserted in the mouth of the patient to catch the prosthetic appliance, filler, etc. coming off during a dental treatment, preventing the prosthetic appliance, filler, etc. from dropping into the trachea or gullet.

4 Claims, 2 Drawing Sheets

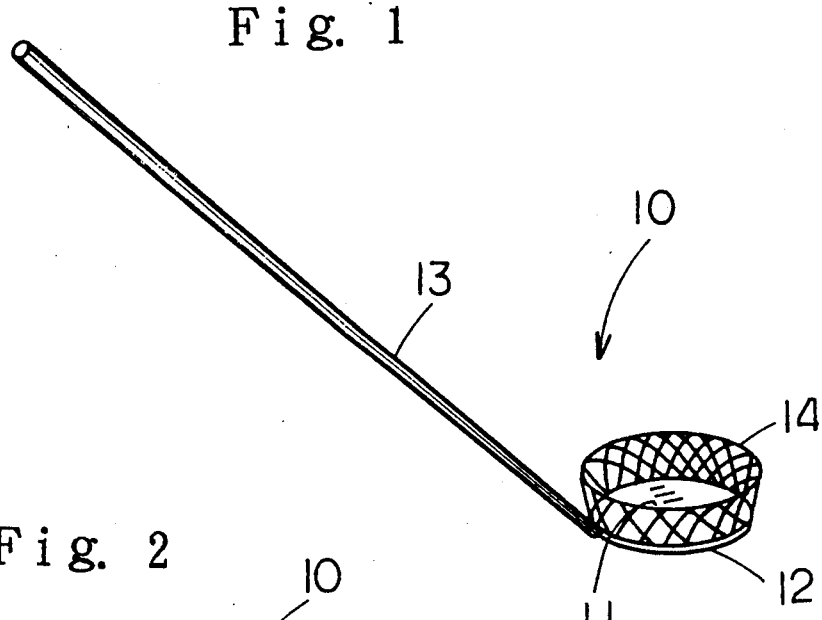
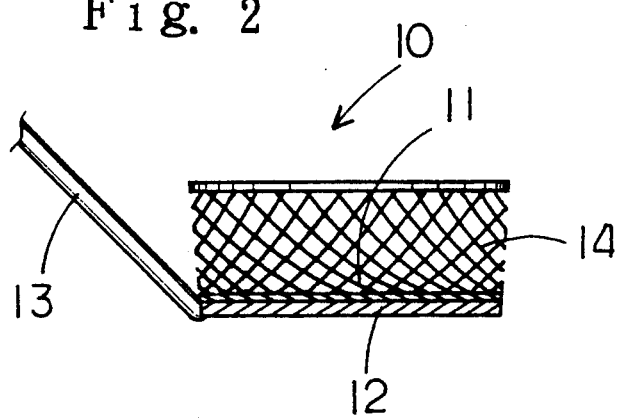
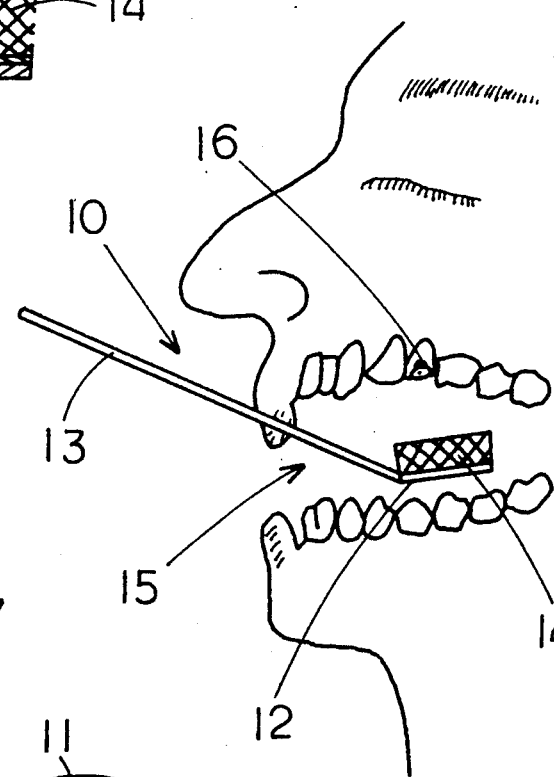
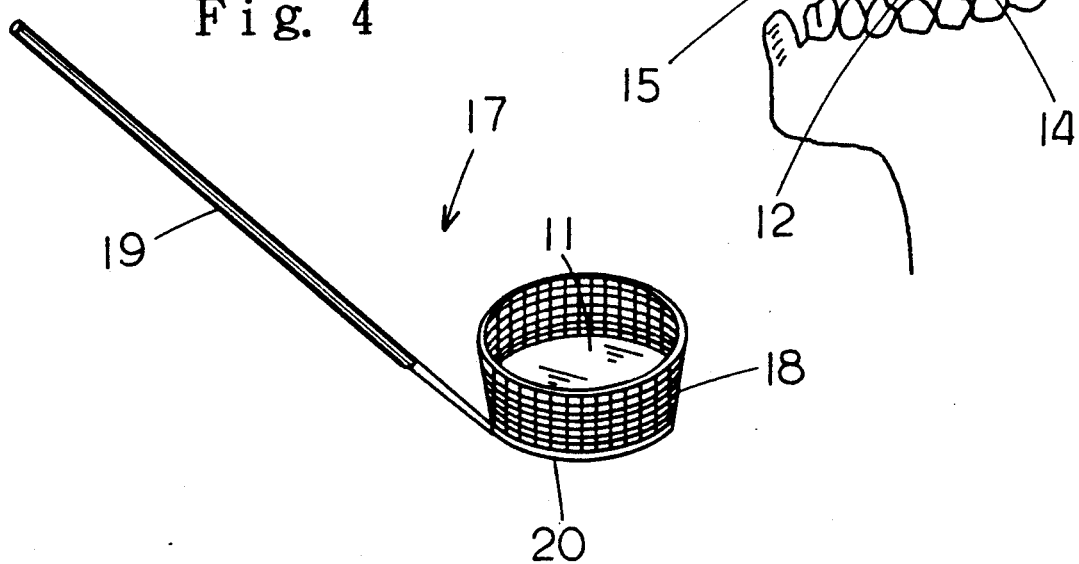

DENTAL INSTRUMENT FOR PREVENTING ACCIDENTAL SWALLOW

FIELD OF THE INVENTION

The present invention relates to a dental instrument to prevent the patient from accidentally swallowing filler or a prosthetic appliance, etc. which is used in dental treatment.

BACKGROUND ART

In dental treatment, it is necessary to attach or detach filler (filling material) or a prosthetic appliance to the tooth or teeth to be treated. The filler or prosthetic applicance may drop into the mouth, of the patient because they are attached or detached by hand. In such a cse, then can be sucked up by pump, etc. if they are small in size, but sometimes an accident can occur in which the trachea is clogged by accidently swallowing the filler, etc. or aspiration.

Another type of accident which can occur is due to using a reamer, etc. which is used in treating a pulp canal which can be dropped into the mouth during the treatment.

During a dental treatment, a dental mirror is used to examine the inside of the mouth. This dental mirror consists of a small circular mirror to which a grip is attached for holding the mirror.

This dental mirror, however, is only for examining the inside of the mouth and not able to catch the above-mentioned filler, prosthetic appliance, etc.

SUMMARY OF THE INVENTION

The present invention has been made in view of abovementioned circumstances and, accordingly, it is an object of this invention to provide a dental instrument which prevents the patient from accidentally swallowing filler, etc. and which is able not only to serve as a dental mirror but to prevent the patient for accidentally swallowing the filler, prosthetic appliance, etc.

The dental instrument for preventing accidental swallow relating to the first invention with the object mentioned above comprises a receiving plate having a mirror on the top face. A circumferential wall which prevents objects from falling into the patient's mouth, is mounted on the periphery of the receiving plate. A grip is attached to the receiving plate or to the circumferential wall.

For the first invention, because a circumferential wall is provided on the periphery of the receiving plate, and a grip is provided on the receiving plate or circumferential wall, it becomes possible to set the dental instrument at the intended position in the mouth to prevent the patient from accidentally swallowing an object by holding the grip and is also possible to catch, the filler, prosthetic appliance, etc. using the receiving plate for the tooth to be treated if objects drop into the mouth, preventing, as a result, the patient from swallowing or aspirating.

Because a mirror is provided on the top face of the receiving plate, it is also possible to examine the back side of the tooth by using the mirror.

The dental instrument relating to the second invention with the object mentioned above comprises a receiving plate having a mirror on the top face. A circumferential wall is mounted on the periphery of the receiving plate. A grip is attached to the receiving plate or the circumferential wall. A setting jig is disposed on the top section of the circumferential wall.

For the dental instrument relating to the second invention, as well as the function and effect mentioned above, because there provided a setting jig on the top section of circumferential wall, the receiving plate can be settled at an intended position by putting the setting jig, for example, on the tooth of the lower jaw. It therefore becomes possible to catch, using the receiving plate, the filler or, prosthetic appliance, etc. dropping toward the throat.

For the first and second inventions, the circumferential wall is preferable to be made of wire net, but it is also possible to use a metal or plastic plate for the circumferential wall. In such a case, it is preferable to provide draining holes through the circumferential wall at the bottom portion of its side face, because saliva, etc. stay on the top surface of the receiving plate.

BRIEF DESCRIPTION OF THE DRAWINGS

FIG. 1 is a diagrammatic perspective view of a dental instrument relating to the first embodiment of the present invention;

FIG. 2 is a sectional view with a portion omitted of the dental instrument for preventing accidental swallow;

FIG. 3 is a diagramatic side view of the dental instrument showing how it is used;

FIG. 4 is a perspective view of a dental instrument relating to the second embodiment;

DETAILED DESCRIPTION OF THE EMBODIMENT

Figure 5:
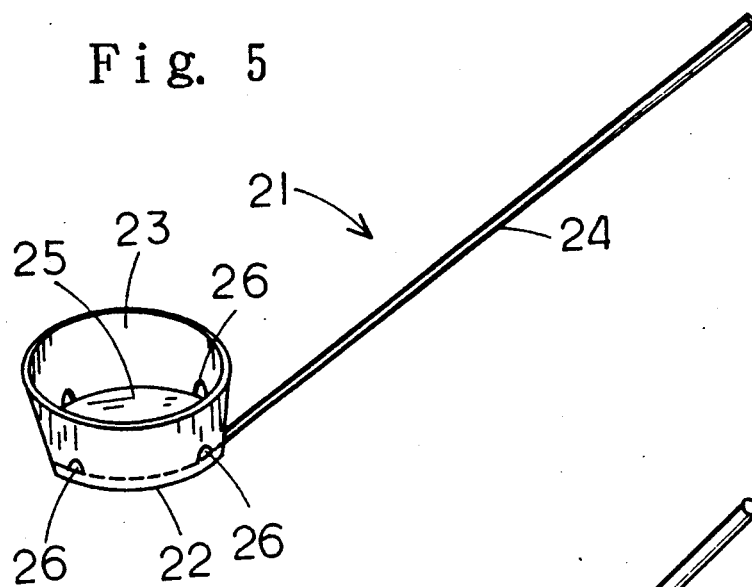
FIG. 5 is a perspective view of a dental instrument relating to the third embodiment.

As shown in FIGS. 1 and 2, the dental instrument 10 for preventing accidental swallow relating to the first embodiment of the invention comprises a receiving plate 12 whose top face is provided with a mirror 11, a grip 13 which is attached to the one side of the receiving plate 12, and a circumferential wall 14 which is mounted on the periphery of the receiving plate 12. The details of these components will be described hereinunder.

The receiving plate 12, grip 13, and the circumferential wall 14 which are the components of the dental instrument 10 to prevent accidentally swallowing objects are made of corrosion-proof metal (such as stainless steel or brass) or plastic. The receiving plate 12 is approximately 10~45 mm in diameter and is provided with a mirror 11 on the top face. The mirror 11 may be either an independent one attached on the receiving plate 12 or one formed directly from the top surface of the receiving plate 12 by speculum treatment.

On one side of the receiving plate 12, an integrated- or attached-type grip 13 is disposed. Though this grip 13 has a straight body in the embodiment, it is pososible to provide concaves and convexes for slip prevention around the body and to form a hook or hole in the grip for hanging.

On the periphery of the receiving plate 12, there is mounted a circumferential wall 14 made of stainless steel. The circumferential wall 14 is 3~10 mm height according to the diameter (10~45 mm) of the mirror 11 and is constructed to spread a little toward the top.

It is also possible to attach another circumferential wall made of a different material such as transparent plastic, colored semitransparent plastic, opaque plastic, or metal in place of the circumferential wall 14 made of wire net and, in such a case, the circumferential wall may be of either net or plate.

In actual use of the dental instrument 10 for preventing accidentally swallowing objects, it is set at the intended position in the mouth 15 with the grip 13 being held by hand as shown in FIG. 3, and then a dental treatment is carried out. In this treatment, if the circumferential wall 14 is made of wire net or transparent plastic used, the back side of the tooth 16 to be treated can be examined in the mirror 11, because the wall has transparency.

If the filler, prosthetic appliance, etc. come off during treatament, they drop onto the receiving plate 12 and are caught there and taken out of the mouth because a circumferential wall 14 is provided on the periphery of the receiving plate 12 for drop prevention.

Details will be described hereinunder on the dental instrument for preventing accidentally swallowed objects relating to the second, third, and fourth embodiments shown in FIGS. 4 through 7, and the same components are provided with the same numerals and the descriptions of these components are omitted.

For the dental instrument 17 for preventing accidentally swallowing objects relating to the second embodiment of the invention shown in FIG. 4, the circumferential wall 18 is made of a stainless steel wire net having relatively fine mesh and, as a result, even fine filler or the chips of a prosthetic appliance can be caught with the receiving plate 20. A relatively larger diameter of the grip 19 at the holding position makes it easy to hold.

FIG. 5 shows the dental instrument 21 for preventing accidentally swallowing objects relating to the third embodiment of the invention and, in this case, the receiving plate 22, the circumferential wall 23, and the grip 24 are made of plastic (synthetic resin), and a mirror 25 is formed on the top surface of the receiving plate 22 by speculum treatment. This makes it easy to manufacture and makes it possible to manufacture the dental instrument 21 for preventing accidentally swallowing objects at low cost. Since the circumferential wall is made of plate-like material in this dental instrument 21, draining holes 26 are provided at the bottom portion of the circumferential wall 23 so as to drain saliva, etc. staying in the instrument.

Figure 6:
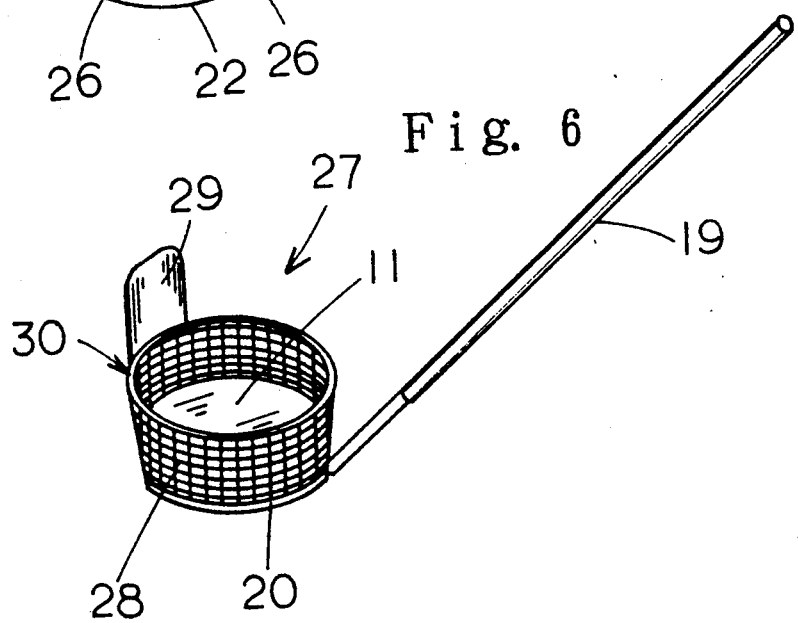
FIG. 6 is a perspective view of a dental instrument relating to the fourth embodiment.
Figure 7:
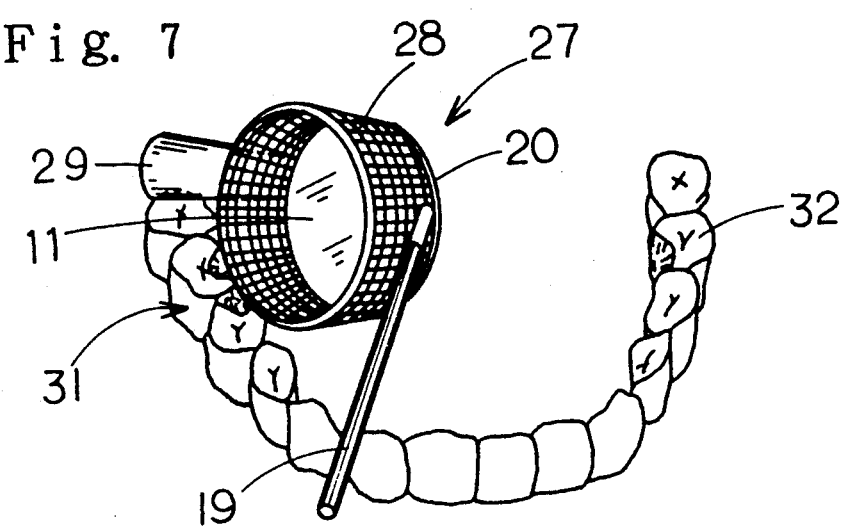
FIG. 7 is a dragamatic prespective view showing how the dental instrument is used.

FIGS. 6 and 7 show the dental instrument 27 for preventing accidental swallow relating to the fourth embodiment of the present invention and, as shown in the figures, there provided a setting jig 29 on the top section of the circumferential wall 28.

This setting jig 29 is attached on the top section of the circumferential wall 28 (having 3~20 mm height) which is mounted on the periphery of the receiving plate 20.

This setting jig 29 is made of corrosion-resistant metal or plastic and attached with clockwise or counterclockwise drift on the opposite side 30 from the grip 19.

Accordingly, in the use of this dental instrument 27 for preventing accidentally swallowing objects as shown in FIG. 7, the instrument is put into the mouth at the intended position with the grip 19 being held by hand and, in this case, either one side of the setting jig is contacted to the top face of the tooth 31 on the lower jaw, and then the treatment of the tooth 31 is carried out. If the filler, prosthetic appliance, etc. come off during the treatment, they drop onto the circumferential wall 28 or the receiving plate 20 on the surface of which a mirror 11 is formed and are taken out of the mouth. Thus accidentally swallowing an object can be prevented.

In FIG. 7, the dental instrument 27 for preventing accidentally swallowing an object is set to the left side tooth 31 and, in the case of treatment on the right side tooth 32, the setting jig 29 is positioned symmetrically to the position mentioned in the fourth embodiment based on the opposite side 30 of the grip 19.

In addition, in the case of the embodiment, it is possible to prevent accidentally swallowing of filler, prosthetic appliance, etc. during the treatment for both right and left teeth on the lower jaw by use of only one dental instrument for preventing accidentally swallowing the object by having a swivel grip which can be turned at the connection to the receiving plate.

Though the grip is directly attached to the receiving plate in above the each embodiment, it is also possible to attach the grip to the circumferential wall.

What is claimed is:

1. A dental instrument for preventing accidental swallow comprising:
    a receiving plate having a mirror on a top face;
    a circumferential wall for drop prevention fixedly mounted on a periphery of said receiving plate, said circumferential wall having holes at least at a bottom thereof where mounted on said receiving plate; and
    a grip attached to one of the receiving plate and the circumferential wall.

2. A dental instrument for preventing accidental swallow set forth in claim 1, wherein the circumferential wall is made of wire net.

3. A dental instrument for preventing accidental swallow comprising:
    a receiving plate having a mirror on the top face;
    a circumferential wall for drop prevention which is made of wire net and mounted on a periphery of said receiving plate; and
    a grip attached to one of the receiving plate and the circumferential wall.

4. A dental instrument for preventing accidental swallow comprising:
    a receiving plate haivng a mirror on the top face;
    a circumferential wall for drop prevention which is made of wire net and mounted on a periphery of said receiving plate;
    a grip attached to one of the receiving plate and the circumferential wall; and
    a setting jig disposed on a top section of abovesaid circumferential wall.

* * * * *